United States Patent [19]

Suami

[11] 4,103,082
[45] Jul. 25, 1978

[54] AMINOCYCLITOL DERIVATIVES AND PROCESS FOR PRODUCING THE SAME

[76] Inventor: Tetsuo Suami, No. 5-8, Naka-machi 3-chome, Musashino-shi, Tokyo, Japan

[21] Appl. No.: 730,396

[22] Filed: Oct. 7, 1976

[30] Foreign Application Priority Data

Oct. 7, 1975 [JP] Japan .................................. 50-120286
Nov. 17, 1975 [JP] Japan .................................. 50-137222

[51] Int. Cl.$^2$ ........................................... C07H 15/22
[52] U.S. Cl. ..................................... 536/17; 424/180; 536/4; 536/18
[58] Field of Search ........................... 536/17, 10, 4, 18

[56] References Cited

U.S. PATENT DOCUMENTS

| 3,929,762 | 12/1975 | Umezawa et al. | 536/17 |
| 3,963,695 | 6/1976 | Cooper et al. | 536/17 |
| 4,020,269 | 4/1977 | Hiraga et al. | 536/10 |

Primary Examiner—Johnnie R. Brown
Attorney, Agent, or Firm—Sughrue, Rothwell, Mion, Zinn and Macpeak

[57] ABSTRACT

Aminocyclitol derivatives, 5-deoxyneamine and 6-deoxyneamine, having antimicrobial activities against various antibiotic-resistant microorganisms, a process for producing 5-deoxyneamine and 6-deoxyneamine and intermediates useful in producing the aminocyclitol derivatives.

4 Claims, No Drawings

AMINOCYCLITOL DERIVATIVES AND PROCESS FOR PRODUCING THE SAME

BACKGROUND OF THE INVENTION

1. Field of the Invention

This invention relates to aminocyclitol derivatives, 5-deoxyneamine and 6-deoxyneamine, having antimicrobial activities. More particularly, this invention relates to 5-deoxyneamine of the formula (Ia):

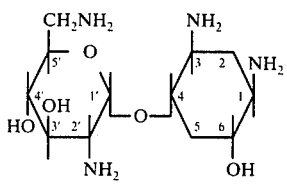

and 6-deoxyneamine of the formula (Ib):

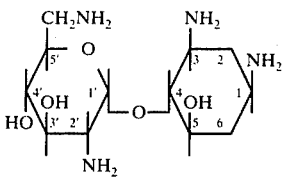

as well as a process for producing 5-deoxyneamine and 6-deoxyneamine and intermediates useful in the process.

2. Description of the Prior Art

It is well known that 3',4'-deoxyneamine which is a 3',4'-deoxy form of neamine exhibits antimicrobial activities against various antibiotic-resistant microorganisms as reported in J. Antibiotics, 24 (10) 711, (1971).

Investigations have now been made on aminocyclitol derivatives having antimicrobial activities on antibiotic-resistant microorganisms and it has been found that neamine having a deoxy structure in the deoxystreptamine moiety is also effective against antibiotic-resistant microorganisms.

SUMMARY OF THE INVENTION

An object of the present invention is to provide aminocyclitol derivatives, 5-deoxyneamine and 6-deoxyneamine, having the formulae (Ia) and (Ib), respectively, having antimicrobial activities.

Another object of this invention is to provide aminocyclitol derivatives having the formula (IV) which are useful as starting materials for producing 5-deoxyneamine and 6-deoxyneamine.

A further object of the present invention is to provide a process for producing 5-deoxyneamine and 6-deoxyneamine from aminocyclitol derivatives having the formula (IV).

A still further object of the present invention is to provide a process for producing aminocyclitol derivatives having the formula (IV) from a compound of the formula (V) hereinafter described.

This invention, therefore, provides aminocyclitol derivatives, 5-deoxyneamine and 6-deoxyneamine, having the formulae (Ia) and (Ib):

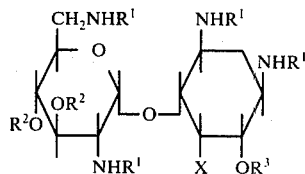

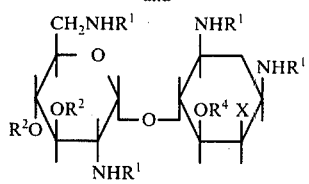

In another embodiment, this invention provides a process for producing the above aminocyclitol derivatives, of the formulae (Ia) and (Ib) by halogenating a compound of the formula (IV):

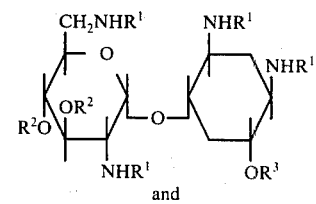

wherein $R^1$ represents a protective group for an amino group, $R^2$ represents a protective group for a hydroxy group, and $R^3$ and $R^4$ each represents a hydrogen atom or an acyl group, with the proviso that both $R^3$ and $R^4$ cannot be simultaneously a hydrogen atom or simultaneously an acyl group, to produce compounds of the formulae (IIIa) and (IIIb):

$$\text{(IIIa)}$$

[structure: CH$_2$NHR$^1$, O, NHR$^1$, OR$^2$, R$^2$O, NHR$^1$, X, OR$^3$]

and $$\text{(IIIb)}$$

[structure: CH$_2$NHR$^1$, O, NHR$^1$, OR$^2$, R$^2$O, OR$^4$ X, NHR$^1$]

wherein $R^1$, $R^2$, $R^3$ and $R^4$ are as defined above, and X represents a halogen atom, dehalogenating the resulting compounds of the formulae (IIIa) and (IIIb) by reduction to produce compounds of the formulae (IIa) and (IIb):

$$\text{(IIa)}$$

[structure: CH$_2$NHR$^1$, O, NHR$^1$, OR$^2$, R$^2$O, NHR$^1$, OR$^3$]

and

-continued

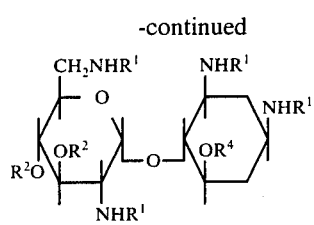
(IIb)

wherein $R^1$, $R^2$, $R^3$ and $R^4$ are as defined above, and removing the amino and hydroxy protective groups.

In an even further embodiment, this invention provides aminocyclitol derivatives of the formulae:

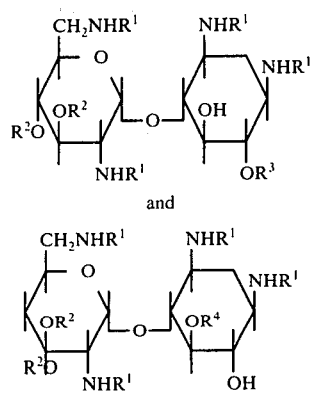

wherein $R^1$ represents a protective group for an amino group; $R^2$ represents a protective group for a hydroxy group; and $R^3$ and $R^4$ each represents a hydrogen atom or an acyl group, with the proviso that both $R^3$ and $R^4$ cannot be simultaneously a hydrogen atom or simultaneously an acyl group, useful in preparing the above aminocyclitol derivative of the formulae (Ia) and (Ib).

DETAILED DESCRIPTION OF THE INVENTION

5-Deoxyneamine and 6-deoxyneamine having the formulae (Ia) and (Ib) above, respectively, can be prepared by halogenating the hydroxy groups of a compound represented by the formula (IV):

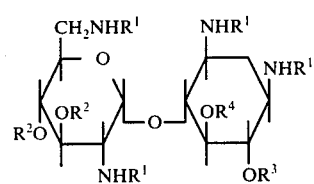
(IV)

wherein $R^1$ represents a protective group for an amino group, $R^2$ represents a protective group for a hydroxy group, and $R^3$ and $R^4$ each represents a hydrogen atom or an acyl group, with the proviso that both $R^3$ and $R^4$ cannot simultaneously be a hydrogen atom or simultaneously be an acyl group, subjecting the resulting compound to dehalogenation by reduction and removing the remaining protective groups.

The starting material having the formula (IV) above is also an aminocyclitol derivative which is novel and includes the following two types of compounds represented by the formulae (IVa) and (IVb), respectively.

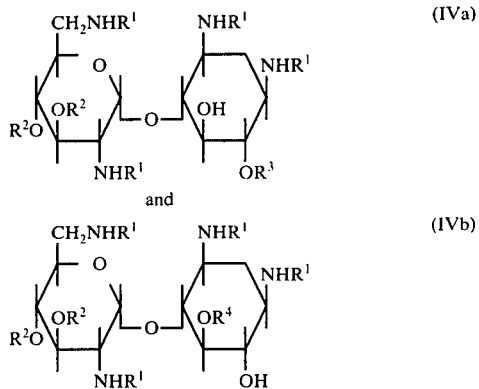

wherein $R^1$, $R^2$, $R^3$ and $R^4$ are as defined above.

Suitable examples of starting materials of the formula (IV) are those having the following groups, but the present invention is not to be construed as being limited to the use of the starting materials having these specific groups: $R^1$: an alkoxycarbonyl group, particularly an alkoxycarbonyl group having 1 to 4 carbon atoms, such as a methoxycarbonyl group, an ethoxycarbonyl group, a propoxycarbonyl group, an isopropoxycarbonyl group and a butoxycarbonyl group; an aryloxycarbonyl group such as a phenoxycarbonyl group and a p-nitrophenoxycarbonyl group; and an aralkoxycarbonyl group such as a benzyloxycarbonyl group, a p-methoxybenzyloxycarbonyl group, a p-ethoxybenzyloxycarbonyl group, a p-chlorobenzyloxycarbonyl group and a p-nitrobenzyloxycarbonyl group; $R^2$: an acyl group such as an acetyl group, a propionyl group and a butyryl group; an aroyl group such as a benzoyl group, a p-chlorobenzoyl group and a p-nitrobenzoyl group; a hemiacetal or hemiketal group such as a tetrahydropyranyl group or a 1-methoxycyclohexyl group; an alkoxycarbonyl group such as an ethoxycarbonyl group, a t-butoxycarbonyl group and a t-amyloxycarbonyl group; and an aralkoxycarbonyl group such as a benzyloxycarbonyl group, a p-methoxybenzyloxycarbonyl group, a p-ethoxybenzyloxycarbonyl group and a p-chlorobenzyloxycarbonyl group; $R^3$ and $R^4$: a hydrogen atom, an acetyl group, a propionyl group, a butyryl group, a valeryl group and the like.

The process for producing 5-deoxyneamine and 6-deoxyneamine in accordance with the process of this invention can be illustrated by the following reaction scheme:

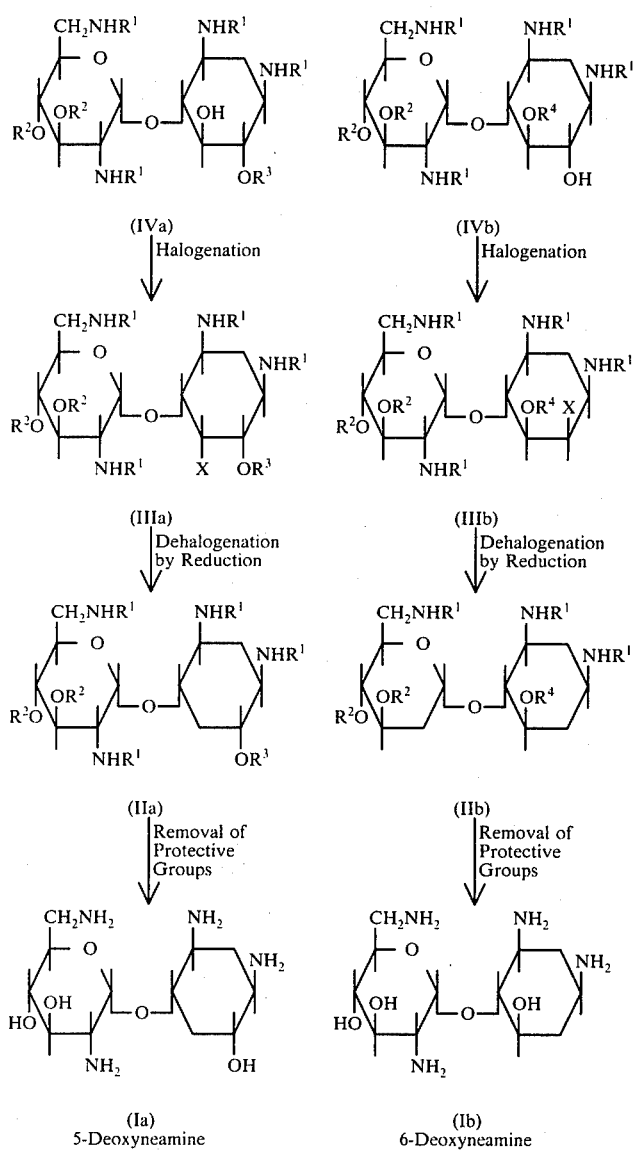

(Ia) 5-Deoxyneamine  (Ib) 6-Deoxyneamine wherein $R^1$, $R^2$, $R^3$ and $R^4$ are as defined above, and X represents a halogen atom.

The halogenation of the starting material of the formula (IVa) or (IVb) in the first step of the process of this invention can be carried out using a halogenating agent in the presence of a neutral or basic solvent which is inert to the starting material and the product obtained, for example, pyridine, benzene, dimethylformamide, tetrahydrofuran, acetonitrile, dioxane or the like. Suitable examples of halogenating agents which can be used in the present invention include sulfuryl chloride, thionyl chloride, phosphorus oxychloride, phosphorus thiooxychloride, pyridium chloride, oxalyl chloride, pyridium bromide, trimethoxymethyl phosphonium iodide, phosphorus pentachloride, phosphorus pentabromide, halosilanes (e.g., trimethylsilyl chloride, dimethyl dichlorosilane and phenyldimethylsilyl chloride) and the like. The halogenating agent is preferably used at a concentration of about 1 to about 30% by weight in the solvent used, and can be used in an approximately equimolecular amount relative to the compound of formula (IV). The halogenation is carried out at a temperature of about −30° to about +150° C, preferably −10° to +50° C, for a period of time of about 30 minutes to about 10 hours.

The thus obtained halogenated compound of the formula (III) is then subjected to a dehalogenation reaction in the second step.

The dehalogenation reaction can be carried out by either a catalytic reduction or a reduction using a reducing agent.

The catalytic reduction can be carried out by bubbling hydrogen gas into a solution of the compound of formulae (IIIa) or (IIIb) in the presence of a catalyst such as a Raney nickel, palladium carbon, platinum oxide, cobalt, rhodium complex, iron and copper. Suitable examples of solvents for the solution of the compound (IIIa) or (IIIb) are water, methanol, ethanol, isopropanol, acetone, dioxane, dimethylformamide, tetrahydrofuran or the like. This catalytic reduction can be conducted at a temperature of about −20° to about +130° C, preferably at a temperature from room temperature to 100° C. The catalytic reduction can be carried out under atmospheric pressure, and can be conducted under pressurized conditions, e.g., at a pressure of about 2 to about 50 kg/cm². The reaction can be performed more smoothly in the presence of a base such as triethylamine and a basic anion exchange resin, e.g., Amberlite IR-45 (trade name, produced by Rohm & Haas Co.).

The reduction of the compound having the formula (IIIa) or (IIIb) using a reducing agent can be carried out in a solution of the compound (IIIa) or (IIIb) dissolved in a solvent such as methanol, ethanol, dimethylformamide, dioxane, tetrahydrofuran, benzene, toluene, dimethylsulfoxide, ethylene glycol and the like, at a temperature of from about $-20°$ to about $+150°$ C, preferably from room temperature to 100° C for about 1 to about 12 hours.

The reducing agents which can be used for this purpose include tributyltin hydride, lithium aluminum hydride, sodium borohydride, lithium, sodium and the like. These reducing agents can be used in an amount of from 1 to 20 mols, preferably 5 to 15 mols, per mol of the compound of the formula (IIIa) or (IIIb).

Advantageously, the reduction with the above reducing agent can be carried out in the presence of a radical initiator such as $\alpha,\alpha'$azo-bis-isobutyronitrile in order to promote the reduction reaction. Also, better results can be obtained by conducting the reduction reaction in an inert atmosphere such as nitrogen gas.

The thus obtained deoxy derivative (IIa or IIb) is then subjected to removal of protective groups in a third step.

The removal of protective groups can be conducted by hydrolyzing the deoxy derivative in the presence of a catalyst such as an acid, e.g., hydrochloric acid, sulfuric acid, etc., or an alkali, e.g., barium hydroxide, sodium hydroxide, potassium hydroxide, sodium alkoxide, potassium alkoxide, ammonia, hydrazine, etc., to obtain 5-deoxyneamine (Ia) or 6-deoxyneamine (Ib).

The hydrolysis can be carried out using the above acid or alkali in an amount of from 7 to 70 mols, preferably 15 to 50 mols, per mol of the compound of the formula (IIa) or (IIb) in a solvent such as methanol, ethanol, aqueous methanol and aqueous ethanol at a temperature of from 30° to 150° C, preferably 50° to 120° C, for a period of 1 to 120 hours, preferably 3 to 100 hours.

The resulting compound (Ia or Ib) can be isolated and purified using a purification such as ion exchange column chromatography using a weakly acidic resin, for example, Amberlite CG-50 and Amberlite CG-120 (trade names, produced by Rohm & Haas Co.).

The compound represented by the formulae (IVa) and (IVb) the starting materials used in this invention, can readily be prepared from neamine described in S. A. Waksman & H. A. Lechevalier Science, 109 305 (1949).

In a preferred embodiment, each amino group of neamine is first substituted with an alkoxycarbonyl group, e.g., an ethoxycarbonyl group, to obtain tetra-N-alkoxycarbonylneamine represented by the general formula (IX):

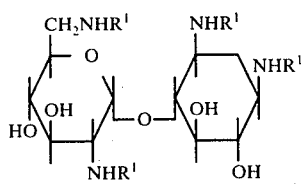

wherein $R^1$ represents an alkoxycarbonyl group.

Then, the thus obtained compound represented by the formula (IX) is treated with cyclohexanone dimethyl ketal to prepare 6,6-O-cyclohexylidene-1,3,2',6'-tetra-N-alkoxycarbonylneamine in which the highly reactive 5,6-positions are substituted with a cyclohexylidene group, represented by the formula (VIII):

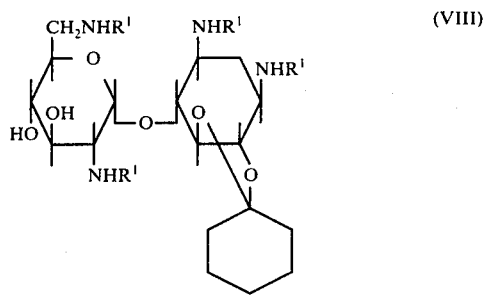

wherein $R^1$ represents an alkoxycarbonyl group.

Subsequently, the above compound (VIII) is acetylated with acetic anhydride to obtain 5,6-cyclohexylidene-3',4'-di-O-acetyl-1,3,2',6'-tetra-N-alkoxycarbonylneamine represented by the formula (VII):

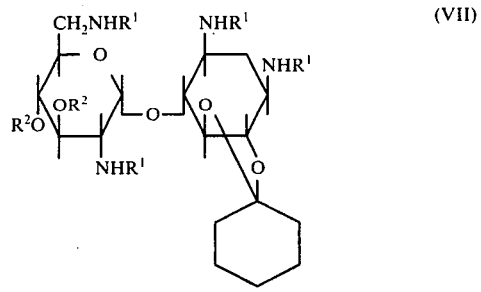

wherein $R^1$ represents an alkoxycarbonyl group and $R^2$ represents an acetyl group.

The cyclohexylidene group as a protective group is then removed from the above compound (VII) to obtain the corresponding compound having hydroxy groups at 5- and 6-positions, and the resulting 5,6-dihydroxy compound is then reacted with a compound represented by the formula (VI) (VIa or VIb):

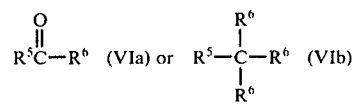

wherein $R^5$ represents an alkyl groyp or an aryl group; and $R^6$ represents an alkoxy group or an aryloxy group, to obtain a compound represented by the formula (V):

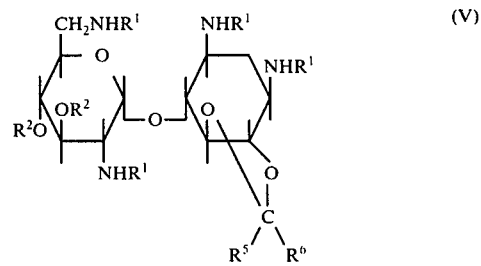

wherein $R^1$, $R^2$, $R^5$ and $R^6$ are as defined above.

The starting compounds (IVa) and (IVb) used in this invention can be prepared by treating the above compound (V) with an acid or an acidic cation exchange resin.

Suitable examples of $R^5$ are an alkyl group having 1 to 4 carbon atoms such as a methyl group, an ethyl group, a propyl group, an isopropyl group, a butyl group and the like and an aryl group such as a phenyl group. Suitable examples of $R^6$ are an alkoxy group such as a methoxy group, and ethoxy group, an n-propoxy group, an isopropoxy group, an n-butoxy group a sec-butoxy group, a t-butoxy group and the like, an aralkoxy group such as a benzyloxy group and an aryloxy group such as a phenoxy group.

The compound of the formula (V) can easily be obtained from neamine in accordance with the above schematic using techniques well known in the art, which are described more specifically below.

That is, neamine is first dissolved in a solvent such as a mixture of acetone and water and an alkoxycarbonyl chloride such as ethoxycarbonyl chloride is added dropwise to the solution to obtain a compound of the formula (IX) in which the amino groups are protected with alkoxycarbonyl groups.

The resulting compound of the formula (IX) is then reacted with cyclohexanone dimethyl ketal in an appropriate solvent such as dimethylformamide under acidic conditions to obtain a compound of the formula (VIII) having a cyclohexylidene group at the highly reactive 5,6-positions.

The resulting compound of the formula (VIII) is then acetylated using, for example, acetic anhydride, under anhydrous conditions in an anhydrous organic solvent such as pyridine to obtain a compound of the formula (VII) where the 3',4'-hydroxy groups are acetylated.

The cyclohexylidene protective groups are then removed from the compound of the formula (VII) by heating the compound (VII) in aqueous acetic acid at about 80° C for about 1 to 2 hours thereby yielding the corresponding compounds having free hydroxy groups at the 5,6-positions.

The resulting compound of the formula (VII) is then reacted with a compound of the formula (VI) (VIa or VIb):

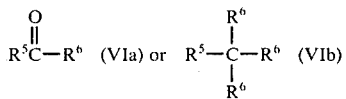

wherein $R^5$ and $R^6$ are as defined above, in an organic solvent such as dimethylformamide in the presence of an acid such as n-toluenesulfonic acid at an elevated temperature, e.g., about 80° C, to obtain a compound of the formula (V). Representative examples of compounds having the formula (IV) are those having a methyl group, an ethyl group or a phenyl group for $R^5$ and those having an ethyl group for $R^6$. A typical example of the compound of the formula (VI) is triethyl orthoacetate.

The resulting compound of the formula (V) is then treated with an acid or an acidic cation exchange resin to obtain the starting material of the present invention having the formula (IV). This treatment can be carried out by dissolving the compound of the formula (V) in an organic solvent such as methanol, ethanol, acetone, chloroform and the like. Any type of acids can be used in the present invention so long as the acid is used in a dilute concentration, for example, at a concentration of 20 to 80% if acetic acid is used. Particularly suitable acids which can be used in the acid treatment are organic acids such as formic acid, acetic acid, propionic acid, lactic acid, benzoic acid, p-toluenesulfonic acid and the like and inorganic acids such as dilute hydrochloric acid, dilute sulfuric acid and the like. The treatment can be effected at a temperature of about $-10°$ to about $+50°$ C for a period of about 0.1 to about 5 hours.

Suitable acidic cation exchange resins include a sulfonated type of a styrene-divinylbenzene copolymer, for example, Amberlite IR-120 (H Type, trade name, produced by Rohm & Haas Co.), Diaion (H Type, trade name, produced by Mitsubishi Chemical Industries, Ltd.) and the like. The acidic cation exchange resins are preferably used in an amount of about 10 to 100% by weight based on the amount of the compound of the formula (V).

5-Deoxyneamine and 6-deoxyneamine of the present invention having the formulae (Ia) and (Ib), respectively, can be acetylated to obtain the corresponding acetylated compound which also exhibits antimicrobial activities. This acetylation of 5-deoxyneamine and 6-deoxyneamine can be effected in an organic solvent such as methanol, ethanol, pyridine and the like using a conventional acetylation procedure, as illustrated in Reference Examples 4 and 5 hereinafter described.

5-Deoxyneamine and 6-deoxyneamine of the present invention exhibit antimicrobial activities superior to those of the parent compound neamine, as shown in the following Tables 1, 2, 3 and 4. The inhibitory activities were determined at various concentrations of the compounds using the paper disk method against the microorganisms indicated and the numerical values show the inhibitory zone diameter in terms of mm.

TABLE 1

|  | Bacillus subtilis ATCC 6633 | | | E. coli K-12 | | |
| --- | --- | --- | --- | --- | --- | --- |
| Concentration | Neamine | 5-Deoxy-neamine | 6-Deoxy-neamine | Neamine | 5-Deoxy-neamine | 6-Deoxy-neamine |
| ($\gamma$/ml) | | | | | | |
| 2000 | 33.5 | 33.4 | 35.7 | 27.4 | 26.6 | 26.7 |
| 1000 | 31.0 | 30.8 | 33.2 | 25.2 | 24.5 | 25.0 |
| 500 | 28.7 | 28.3 | 31.2 | 22.6 | 22.0 | 21.9 |
| 250 | 25.0 | 25.6 | 28.2 | 20.4 | 18.7 | 20.3 |
| 125 | 23.0 | 23.2 | 25.6 | 17.2 | 17.2 | 18.2 |
| 62.5 | 19.9 | 20.5 | 22.7 | 14.3 | 14.7 | 16.0 |
| 31.2 | 17.0 | 15.7 | 21.1 | 11.4 | 12.1 | 12.9 |
| 15.6 | 14.0 | 13.8 | 17.6 | 0 | 0 | 11.2 |
| 7.8 | 11.5 | 11.2 | 15.0 | 0 | 0 | 0 |

TABLE 2

| Concentration | Staphylococcus aureus 6538P | | | E. coli HL-1629 (Kanamycin-resistant strain) | | |
| --- | --- | --- | --- | --- | --- | --- |
| | Neamine | 5-Deoxy-neamine | 6-Deoxy-neamine | Neamine | 5-Deoxy-neamine | 6-Deoxy-neamine |
| (γ/ml) | | | | | | |
| 2000 | 22.8 | 22.5 | 24.2 | 12.3 | 13.9 | 18.0 |
| 1000 | 20.7 | 20.4 | 22.2 | 0 | 0 | 12.5 |
| 500 | 18.3 | 18.5 | 20.0 | — | — | 0 |
| 250 | 15.3 | 15.3 | 18.1 | — | — | — |
| 125 | 13.0 | 12.4 | 15.7 | — | — | — |
| 62.5 | 10.0 | 10.3 | 12.0 | — | — | — |
| 31.2 | 0 | 0 | 10.0 | — | — | — |
| 15.6 | 0 | 0 | 0 | — | — | — |
| 7.8 | 0 | 0 | 0 | — | — | — |

TABLE 3

| Concentration | Klebsiella 6 | | | Klebsiella 7 | | |
| --- | --- | --- | --- | --- | --- | --- |
| | Neamine | 5-Deoxy-neamine | 6-Deoxy-neamine | Neamine | 5-Deoxy-neamine | 6-Deoxy-neamine |
| (γ/ml) | | | | | | |
| 2000 | 0 | 0 | 16.4 | 0 | 0 | 17.5 |
| 1000 | — | — | 14.1 | — | — | 15.6 |
| 500 | — | — | 11.1 | — | — | 11.2 |
| 250 | — | — | 0 | — | — | 0 |

TABLE 4

| Concentration | Mycobacterium 607 | | | Pseudomonas 1007 | | |
| --- | --- | --- | --- | --- | --- | --- |
| | Neamine | 5-Deoxy-neamine | 6-Deoxy-neamine | Neamine | 5-Deoxy-neamine | 6-Deoxy-neamine |
| (γ/ml) | | | | | | |
| 2000 | 32.5 | 26.8 | 33.6 | 0 | 0 | 0 |
| 1000 | 26.4 | 22.0 | 28.3 | — | — | — |
| 500 | 20.4 | 16.4 | 21.7 | — | — | — |
| 250 | 14.8 | 10.4 | 16.2 | — | — | — |
| 125 | 0 | 0 | 11.0 | — | — | — |
| 62.5 | 0 | 0 | 0 | — | — | — |

Furthermore, the compounds of this invention exhibit following antibacterial activity (Minimum Inhibitory Concentration) where Neomycin A is shown as reference antibiotic.

TABLE 5

| | MIC (μg/ml) | | |
| --- | --- | --- | --- |
| Test Organisms | 6-Deoxy-neamine | 5-Deoxy-neamine | Neomycin A |
| Staphylococcus aureus 209P JC-1 | 1.56 | 0.39 | 0.78 |
| Staphylococcus aureus Smith S-424 | 3.13 | 0.78 | 1.56 |
| Staphylococcus aureus No. 26 | 6.25 | 1.56 | 3.13 |
| Staphylococcus aureus C73-4 | 6.25 | 1.56 | 3.13 |
| Staphylococcus aureus C73-10 | 6.25 | 1.56 | 3.13 |
| Staphylococcus aureus C73-21 | 1.56 | 0.20 | 0.78 |
| Staphylococcus albus PCI-1200A | 3.13 | 0.20 | 0.78 |
| Bacillus subtilis ATCC 6633 | 0.78 | 0.39 | 1.56 |
| Bacillus anthracis No. 119 | 12.5 | 1.56 | 12.5 |
| E. coli C73-1 | 25 | 12.5 | 25 |
| E. coli C73-4 | 25 | 12.5 | 25 |
| E. coli C73-12 | 12.5 | 6.25 | 12.5 |
| Salmonella species C73-30 | 50 | 12.5 | 25 |
| Shigella dysenteriae Shigae | 12.5 | 6.25 | 12.5 |
| Klebsiella pneumoniae | 25 | 6.25 | 12.5 |
| Proteus morganii Kono | 12.5 | 6.25 | 12.5 |
| Proteus species C73-23 | 25 | 12.5 | 25 |
| Proteus species C73-25 | 6.25 | 3.13 | 6.25 |
| Proteus species C73-33 | 100 | 50 | 100 |
| Proteus species C73-34 | 25 | 12.5 | 25 |
| Enterococcus species C73-33 | 25 | 6.25 | 12.5 |
| Enterococcus species C73-17 | 50 | 6.25 | 100 |
| Vibrio parahaemolyticus K-3 | 1.56 | 0.39 | 1.56 |
| Vibrio parahaemolyticus K-5 | 25 | 12.5 | 50 |
| Vibrio parahaemolyticus K-7 | 25 | 12.5 | 50 |

As for the acute toxicity, all male ICR mice were survived at each intravenous administration of 200 mg/kg of 5-deoxyneamine or 6-deoxyneamine.

The present invention is further illustrated by the following Examples and Reference Examples, but they are not to be construed as limiting the present invention.

Unless otherwise indicated, parts, percents, ratios and the like are by weight.

REFERENCE EXAMPLE 1

(1) Preparation of Tetra-1-N-(ethoxycarbonyl)neamine

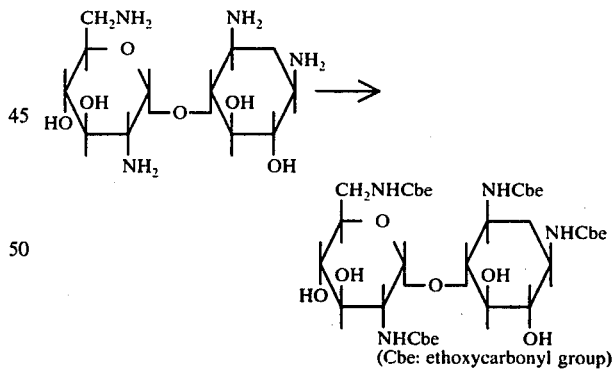
(Cbe: ethoxycarbonyl group)

3.00 g of crude neamine was dissolved in 50 ml of water and the solution was treated with 15 ml of IRA-400(OH$^-$)resin (trade name, produced by Rohm & Haas Co.) for 45 minutes. The resulting filtrate was then concentrated under reduced pressure and the precipitated neamine was dissolved in 60 ml of a mixture of water and acetone (1 : 1 by volume). 7.2 ml(8 mols per mol of neamine) of ethoxycarbonyl chloride was added dropwise to the solution with stirring while cooling with ice and 4.0 g of sodium carbonate was then added to the mixture. The resulting mixture was allowed to react overnight, and the reaction mixture was suction-filtered and the filter cake was washed with a small amount of water and dried under reduced pressure to obtain 4.91 g (86% yield) of the product.

(2) Preparation of 5,6-O-Cyclohexylidene-tetra-N-ethoxycarbonylneamine

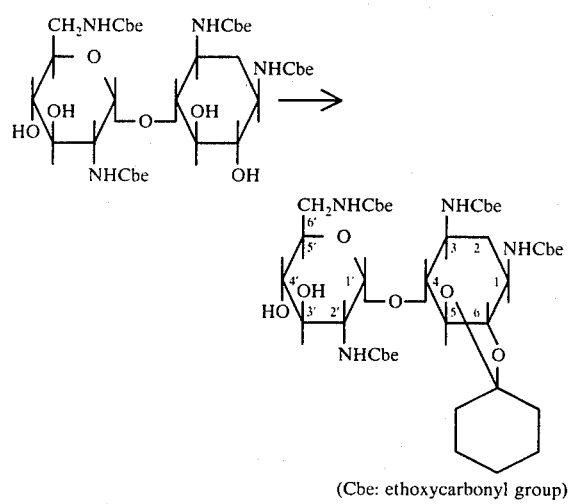

(Cbe: ethoxycarbonyl group)

470 mg of tetra-N-ethoxycarbonylneamine prepared as described in (1) above was suspended in 5 ml of dimethylformamide, and 23 mg of p-toluenesulfonic acid and 1.4 ml of cyclohexanone dimethyl ketal were added to the suspension while keeping the mixture at a temperature of 50° to 60° C under reduced pressure thereby allowing the mixture to react.

After reaction for 2 hours, an aliquot of the reaction mixture was tested by thin layer chromatography to confirm the disappearance of the starting material. The reaction was discontinued after 2.5 hours of total reaction time and allowed to stand at room temperature (about 20° - 30° C) for 15 minutes followed by addition of 2.5 ml of methanol. After allowing the reaction mixture to stand for 3 hours, the disappearance of most of the sub-spots was confirmed by thin layer chromatography and the mixture was rendered neutral with 50 mg of sodium carbonate. The reaction mixture was then evaporated at a temperature below 47° C to obtain a white turbid oil. 10 ml of cold water was added to the oil to obtain a white substance which floated and, after allowing the mixture to stand overnight, it was suction-filtered and dried under reduced pressure to obtain 346 mg (65% yield) of the desired product having a melting point of 183° - 184° C and an optical rotation of $[\alpha]_D^{19} + 35°$ Elemental Analysis: Calc'd for $C_{30}H_{50}N_4O_{14}$: C 52.14; H 7.30; N 8.12; 14; Found: C 51.89; H 7.22; N 7.87.

(3) Preparation of 5,6-Cyclohexylidene-3',4'-di-O-acetyl-1,3,2',6'-tetra-N-(ethoxycarbonyl)neamine

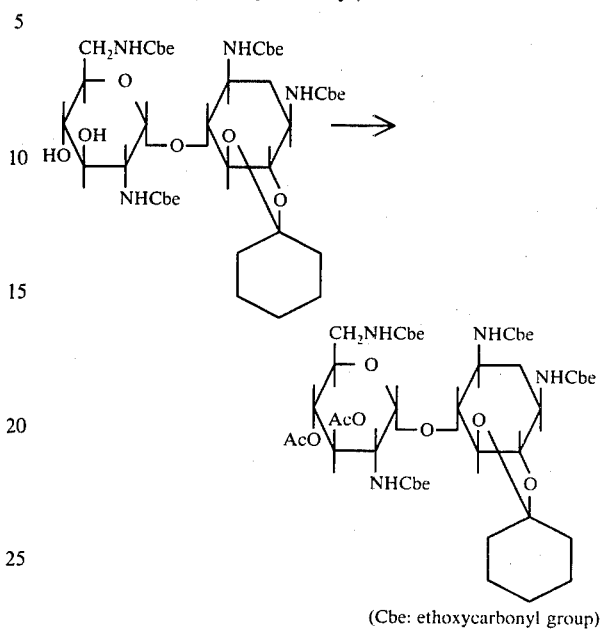

(Cbe: ethoxycarbonyl group)

1.5 g of 5,6-O-cyclohexylidene-1,3,2',6'-tetra-N-(ethoxycarbonyl)neamine prepared as described in (2) above was acetylated with 12 ml of acetic anhydride in 15 ml of anhydrous pyridine. Any insoluble materials remaining in the acetylation reaction mixture were removed by filtration and the solvent was evaporated from the filtrate under reduced pressure. Diethyl ether was then added to the residue to obtain 1.5 g (92% yield) of amorphous crystals having a melting point of 209° - 212° C and an optical rotation of $[\alpha]_D^{21} + 44°$ (C, 1.0 in methanol).

Elemental Analysis: Calc'd for $C_{34}H_{54}N_4O_{16}$: C 52.70; H 7.02; N 7.23; Found: C 52.51; H 7.00; N 6.98.

(4) Preparation of 3',4'-Di-O-acetyl-1,3,2',6'-tetra-N-(ethoxycarbonyl)neamine

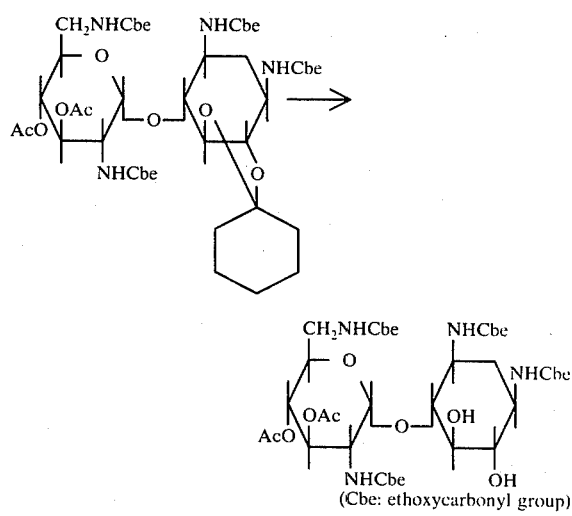

(Cbe: ethoxycarbonyl group)

0.58 g of 5,6-cyclohexylidene-3',4'-di-O-acetyl-1,3,2',6'-tetra-N-(ethoxycarbonyl)neamine was dissolved in 20 ml of 70% aqueous acetic acid. The solution was heated at a temperature of 80° C for 1.5 hours and the solvent was then evaporated under reduced pressure. Diethyl ether was added to the residue to obtain an amorphous powder which was then stored overnight in a refrigerator. The resulting crystals were collected to obtain 0.5 g (96% yield) of a crude product. Recrystallization of the product from methanol yielded 0.44 g (85% yield) of the desired product as crystals having a melting point of 132° - 135° C and an optical rotation of $[\alpha]_D^{21} + 52°$ (C, 1.0 in methanol). The product had the following characteristics.

PMR (CDCl$_3$):
$\delta$1.24 (t, 12, J = 7.0 Hz, 4COCH$_2$C$\underline{H}_3$),
1.99 (s, 3, OAc),
2.03 (s, 3, OAc),
4.08 (q, 8, J = 7.0 Hz, COC$\underline{H}_2$CH$_3$)

Elemental Analysis: Calc'd for C$_{28}$H$_{46}$N$_4$O$_{16}$: C 48.41; H 6.68; N 8.07; Found: C 48.40; H 6.65; N 7.75.

(5) Preparation of 3',4'-Di-O-acetyl-1,3,2',6'-tetra-N-(ethoxycarbonyl)-5,6-O-(ethoxyethylidene)neamine 2.49 g of 3',4'-di-O-acetyl-1,3,2',6'-tetra-N-(ethoxycarbonyl)neamine prepared as described in (4) above was dissolved in 23 ml of dimethylformamide, and 17.3 ml of triethyl orthoacetate was added thereto. The mixture was then heated at a temperature of 70° C for 1 hour in the presence of 78 mg of p-toluenesulfonic acid followed by cooling. The resulting reaction mixture was treated with Amberlite IRA 400 (OH Type, trade name, produced by Rohm & Haas Co.) to remove the acid and the solvent was then removed by evaporation. The residue was dissolved in chloroform and the solution was passed through a column packed with alumina. Chloroform was then removed by evaporation from the column effluent to give 2.64 g (99% yield) of the desired product as a light yellow syrup. The product had the following characteristics.

PMR (CDCl$_3$):
$\delta$1.1 - 1.5 (M, 18, C—CH$_3$, OCH$_2$CH$_3$, 4COOCH$_2$C$\underline{H}_3$),
1.99 (s, 3, OAc),
2.02 (s, 3, OAc)

REFERENCE EXAMPLE 2

2.60 g of 3',4'-O-acetyl-1,3,2',6'-tetra-N-(ethoxycarbonyl)-5,6-O-(ethoxyethylidene)neamine prepared as described in Reference Example 1, (5) was dissolved in 35 ml of 85% acetone, and the solution was stirred for 24 hours in the presence of 1.5 g of Amberlite IR-120 (H Type, trade name, produced by Rohm & Haas Co.) followed by filtration. The solvent was then evaporated from the filtrate under reduced pressure to obtain a glass like solid. The resulting solid was fractionated using a solvent system of chloroform-ethanol (16 : 1 by volume) and a silica gel column (100 g of Wakogel C-300, trade name, produced by Wako Pure Chemical Ind., Ltd.). Fractions having a single spot of R$_f$ 0.41 were collected and the solvent was removed by evaporation. The residue was washed with cyclohexane to obtain 0.58 g (22% yield) of 6,3',4'-tri-O-acetyl-1,3,2',6'-tetra-N-(ethoxycarbonyl)neamine as an amorphous solid having a melting point of 99° - 106° C (no definite melting point) and an optical rotation of $[\alpha]_D^{23} + 64.1°$ (C, 1.03 in chloroform). The product had the following characteristics.

PMR (CDCl$_3$):
$\delta$1.1 - 1.4 (m, 12, 4COOCH$_2$C$\underline{H}_3$),
1.99 (s, 3, OAc),
2.02 (s, 3, OAc),
2.10 (s, 3, OAc)

Elemental Analysis:
Calc'd for C$_{30}$H$_{48}$N$_4$O$_{17}$: C 48.91; H 6.57; N 7.61;
Found: C 48.70; H 6.46; N 7.23.

REFERENCE EXAMPLE 3

Fractions having a single spot of R$_f$ 0.33 as described in Reference Example 2 above were collected and the solvent was removed by evaporation to obtain a crystalline residue. The resulting residue was recrystallized from a solvent system of hexane-methanol (2 : 1 by volume) to give 0.67 g (25% yield) of 5,3',4'-tri-O-acetyl-1,3,2',6'-tetra-N-(ethoxycarbonyl)neamine having a melting point of 206° - 207° C and an optical rotation of $[\alpha]_D^{21} + 33.7°$ (C, 0.83 in chloroform). The product had the following characteristics.

PMR (CDCl$_3$):
$\delta$1.25 (t, 12, J = 7.0 Hz, 4COOCH$_2$C$\underline{H}_3$),
1.99 (s, 3, OAc),
2.02 (s, 3, OAc),
2.05 (s, 3, OAc)

Elemental Analysis:
Calc'd for C$_{30}$H$_{48}$N$_4$O$_{17}$: C 48.91; H 6.57; N 7.61;
Found: C 48.83; H 6.43; N 7.41.

EXAMPLE 1

(1) Preparation of 6,3',4'-Tri-O-acetyl-5-chloro-1,3,2',6'-tetra-N-(ethoxycarbonyl)-5-deoxyneamine 0.31 g of 6,3',4'-tri-O-acetyl-1,3,2',6'-tetra-N-(ethoxycarbonyl)neamine prepared as described in Reference Example 2 was dissolved in anhydrous pyridine and 0.41 ml of sulfuryl chloride was added to the solution at a temperature of −15° C. The mixture was stirred for 3.7 hours while cooling with ice, and 20 ml of chloroform was added thereto. The resulting chloroform solution was washed subsequently with an aqueous sodium hydrogen sulfate solution, an aqueous sodium bicarbonate solution and ice-water, and dried over anhydrous sodium sulfate. The solvent was removed by distillation under reduced pressure and the residue was recrystallized from ethanol to obtain 0.21 g (64% yield) of 6,3',4'-tri-O-acetyl-5-chloro-1,3,2',6'-tetra-N-(ethoxycarbonyl)-5-deoxyneamine as light yellow crystals having a melting point of 128° - 130° C. Repeated recrystallization from ethanol yielded a pure product having a melting point of 130° to 132° C and an optical rotation of $[\alpha]_D^{23} + 81.2°$ (C, 0.83 in chloroform). The product had the following characteristics.

PMR (CDCl$_3$):
$\delta$1.1 - 1.4 (m, 12, 4COOCH$_2$C$\underline{H}_3$),
2.00 (s, 3, OAc),
2.03 (s, 3, OAc),
2.12 (s, 3, OAc)

Elemental Analysis:
Calc'd for C$_{30}$H$_{47}$N$_4$O$_{16}$Cl: C 47.71; H 6.27; N 7.42; Cl 4.69; Found: C 47.68; H 6.16; N 7.14; Cl 4.94.

(2) Preparation of 6,3',4'-O-Tri-O-acetyl-1,3,2',6'-tetra-N-(ethoxycarbonyl)-5-deoxyneamine 175 mg of 6,3',4'-tri-O-acetyl-5-chloro-1,3,2',6'-tetra-N-(ethoxycarbonyl)-5-deoxyneamine was dissolved in 16 ml of anhydrous toluene, and 0.5 ml of tributyltin hydride was added in the presence of 6 mg of α,α-azobis-isobutyronitrile under a nitrogen stream. After allowing the mixture to stand for 2 hours, it was heated at 90° C and the solvent was removed by distillation under reduced pressure. The residue was washed successively with diethyl ether and n-hexane to obtain 183 mg of amorphous powder. The resulting crude powder was dissolved in an acetone-chloroform-ethanol mixture (1.25 : 15 : 1 by volume) and the solution was subjected to silica gel column chromatography to obtain an amorphous solid having a single spot of $R_f$ 0.54 on thin layer chromatography. The product thus obtained was triturated with a mixture of diethyl ether and n-hexane to obtain the desired product, 6',3',4'-tri-O-acetyl-1,3,2',6'-tetra-N-(ethoxycarbonyl)-5-deoxyneamine as an amorphous powder having a melting point of 118° – 122° C and an optical rotation of $[\alpha]_D^{27} + 78°$ (C, 1.02 in chloroform). The product had the following characteristics.

PMR (CDCl$_3$):
δ1.06 – 1.47 (m, 12, 4COOCH$_2$CH$_3$),
2.01 (s, 3, OAc),
2.03 (s, 3, OAc),
2.05 (s, 3, OAc)

Elemental Analysis:
Calc'd for C$_{30}$H$_{48}$N$_4$O$_{16}$: C 49.99; H 6.71; N 7.77;
Found: C 49.69; H 6.61; N 7.47.

(3) Preparation of 5-Deoxyneamine 310 mg of 6,3'4'-tri-O-acetyl-1,3,2',6'-tetra-N-(ethoxycarbonyl)-5-deoxyneamino prepared as described in (2) above was dissolved in 4.0 ml of methanol, and a solution of 2.4 g of barium hydroxide dissolved in 8.0 ml of water was added thereto. The mixture was then heated while refluxing for 6 hours. Carbon dioxide gas was introduced into the mixture and the precipitate formed was removed by filtration. The filtrate was evaporated and the residue was purified with Amberlite CG-50 (NH$_4^+$-Type, trade name, produced by Rohm & Haas Co.). The resin was pretreated with 0.05 N aqueous ammonia and then the elution was with 0.3 N aqueous ammonia to obtain 88 mg (67% yield) of 5-deoxyneamine as a hygroscopic amorphous solid having a melting point of 160° C (with colored decomposition) and $[\alpha]_D^{21} + 128°$ (C, 1.58 in water).

EXAMPLE 2

(1) Preparation of
5,3',4'-Tri-O-acetyl-6-chloro-1,3,2',6'-tetra-N-(ethoxycabonyl)-6-deoxyneamine 0.25 g of 5,3',4'-tri-O-acetyl-1,3,2',6'-tetra-N-(ethoxycarbonyl)neamine prepared as described in Reference Example 3 was reacted with sulfuryl chloride in 7 ml of anhydrous pyridine in the same manner as described in Example 1, (1) to obtain 0.24 g (95% yield) of 5,3',4'-tri-O-acetyl-6-chloro-1,3,2',6'-tetra-N-(ethoxycarbonyl)-6-deoxyneamine as a light brown glass like material having an optical rotation of $[\alpha]_D^{26} + 71.1°$ (C, 0.85 in chloroform). The product had the following characteristics.

PMR (CDCl$_3$):
δ1.1 – 1.4 (m, 12, 4COOCH$_2$CH$_3$),
1.99 (s, 3, OAc),
2.02 (s, 3, OAc),
2.07 (s, 3, OAc)

Elemental Analysis:
Calc'd for C$_{30}$H$_{47}$N$_4$O$_{16}$Cl: C 47.71; H 6.27; N 7.42; Cl 4.69; Found: C 47.39; H 6.09; N 7.25; Cl 4.92.

(2) Preparation of
5,3',4'-Tri-O-acetyl-1,3,2',6'-N-(ethoxycarbonyl)-6-deoxyneamine 240 mg of 5,3',4'-tri-O-acetyl-6-chloro-1,3,2',6'-tetra-N-(ethoxycarbonyl)-6-deoxyneamine was dissolved in 15 ml of ethanol, and the solution was reacted with Raney nickel T-4 in a Parr bomb in the presence of Amberlite IR-45 (OH-Type, trade name, produced by Rohm & Haas Co.) for 20 hours under a pressure of 3.4 kg/cm$^2$. After completion of the reaction, the catalyst was removed by filtration and the filtrate was evaporated. The residue was then fractionated using silica gel (Wakogel C-300, 10 g, trade name, produced by Wako Pure Chemical Ind., Ltd.) column chromatography using a solvent system of benzene-isopropyl alcohol (15 : 1 by volume). Fractions showing a single spot of $R_f$ 0.24 on thin layer chromatography were collected and the solvent was removed by distillation to obtain 160 mg (71% yield) of 5,3',4'-tri-O-acetyl-1,3,2',6'-tetra-N-(ethoxycarbonyl)-6-deoxyneamine having a melting point of 115 to 117° C and an optical rotation of $[\alpha]_D^{26} + 58.3°$ (C, 1.08 in chloroform). The product had the following characteristics.

PMR (CDCl$_3$):
δ1.1 – 1.4 (m, 12, 4COOCH$_2$CH$_3$),
1.98 (s, 3, OAc),
1.99 (s, 3, OAc),
2.01 (s, 3, OAc)

Elemental Analysis:
Calc'd for C$_{30}$H$_{48}$N$_4$O$_{16}$: C 49.99; H 6.71; N 7.77;
Found: C 49.64; H 6.54; N 7.54.

(3) Preparation of 6-Deoxyneamine 0.34 g of 5,3',4'-tri-O-acetyl-1,3,2',6'-N-(ethoxycarbonyl)-6-deoxyneamine and 4.5 g of barium hydroxide were dissolved in 29 ml of 30% aqueous methanol, and the solution was heated while refluxing for 95 hours. The reaction mixture was saturated with carbon dioxide gas, and the precipitated barium carbonate was removed by filtration. The filtrate was evaporated under reduced pressure and the residue was dissolved in a small amount of cold water. The solution was filtered, and the filtrate was evaporated to obtain 291 mg of a glass like solid. The resulting solid was subjected to column chromatography using Amberlite CG-50 (NH$_4^+$, trade name, produced by Rohm & Haas Co.) (4.5 × 330 mm column), and, after pretreatment with 0.05 N aqueous ammonia, the column was eluted with 0.3 N aqueous ammonia to obtain 65 mg (46% yield) of 6-deoxyneamine as an amorphous substance showing a single spot of $R_f$ 0.32 on thin layer chromatography using a solvent system of 28% aqueous ammonia : n-butanol : ethanol : water (7 : 8 : 10 : 5 by volume). The product had an optical rotation of $[\alpha]_D^{22} + 98.8°$ (C, 1.02 in water) and a melting point of 135° C (with bubbling decomposition).

REFERENCE EXAMPLE 4

Preparation of Tetra-N-acetyl-5-deoxyneamine 80 mg of 5-deoxyneamine prepared as described in Example 1 as acetylated with 0.3 ml of acetic anhydride in 6 ml of methanol while cooling with ice. The reaction mixture was allowed to stand overnight in a refrigerator and the solvent was removed by distillation. The resulting residue was washed with isopropyl alcohol to obtain 94 mg (76% yield) of tetra-N-acetyl-5-deoxyneamine as an amorphous solid having a melting point higher than 290° C and an optical rotation of $[\alpha]_D^{21} + 105°$ (C, 1.05 in water). The product had the following characteristics.

PMR (D$_2$O):
  δ1.97 (s, 6, 2XNAc),
  2.01 (s, 6, 2XNAc),
  4.93 (d, 1, J = 3 Hz, H-1')

Elemental Analysis:
Calc'd for C$_{20}$H$_{34}$N$_4$O$_9$: C 50.62; H 7.22; N 11.81; Found: C 50.41; H 7.02; N 11.63.

REFERENCE EXAMPLE 5

Preparation of Tetra-N-acetyl-6-deoxyneamine 48 mg of 6-deoxyneamine prepared as described in Example 2 was acetylated with 1.6 ml of acetic anhydride in 4.5 ml of methanol while cooling with ice. The reaction mixture was allowed to stand overnight in a refrigerator. The precipitate formed was collected by filtration, washed with methanol and dried to obtain 32 mg (43% yield) of tetra-N-acetyl-6-deoxyneamine having a melting point higher than 300° C and an optical rotation of $[\alpha]_D^{22} + 85.1°$ (C, 0.45 in water). The product had the following characteristics.

PMR (D$_2$O):
  δ1.97 (s, 3, NAc),
  2.02 (s, 3, NAc),
  2.04 (s, 3, NAc),
  2.07 (s, 3, NAc),
  5.38 (d, 1, J = 3 Hz, H-1')

Elemental Analysis:
Calc'd for C$_{20}$H$_{34}$N$_4$O$_9$: C 50.62; H 7.22; N 11.81; Found: C 50.30; H 7.02; N 11.67.

While the invention has been described in detail and with reference to specific embodiments thereof, it will be apparent to one skilled in the art that various changes and modifications can be made therein without departing from the spirit and scope thereof.

What is claimed is:

1. 5-Deoxyneamine and 6-deoxyneamine having the formulae (Ia) and (Ib):

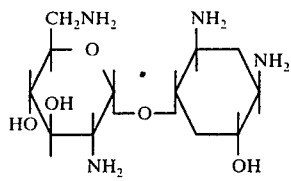

(Ia)

-continued

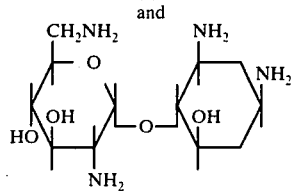

(Ib)

2. Aminocyclito derivatives represented by the formula (IVa) and (IVb):

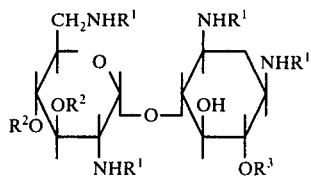

(IVa)

and

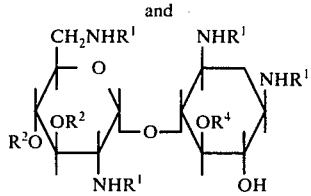

(IVb)

wherein
R$^1$ represents a group selected from the group consisting of methoxycarbonyl, ethoxycarbonyl, propoxycarbonyl, isopropoxycarbonyl, butoxycarbonyl, phenoxycarbonyl, p-nitrophenoxycarbonyl, benzyloxycarbonyl, p-methoxybenzyloxycarbonyl, -p-ethoxybenzyloxycarbonyl, p-chlorobenzyloxycarbonyl or p-nitrobenzyloxycarbonyl;

R$^2$ represents a group selected from the group consisting of acetyl, propinonyl butyryl, benzoyl, p-chlorobenzoyl, p-nitrobenzoyl, tetrahydropyranyl, 1-methoxycyclohexyl, ethoxycarbonyl, t-butoxycarbonyl, t-amyloxycarbonyl, benzyloxycarbonyl, p-methoxybenzyloxycarbonyl, p-ethoxybenzyloxycarbonyl or p-chlorobenzyloxycarbonyl; and R$^3$ and R$^4$ each represents an acetyl group, a propionyl group, a butyryl group or a valeryl group.

3. The aminocyclitol derivatives of claim 2, wherein R$^2$ is selected from the group consisting of acetyl, propionyl or butyryl.

4. The aminocyclitol derivatives of claim 2, wherein R$^3$ and R$^4$ are acetyl.

* * * * *